(12) United States Patent
Vaske et al.

(10) Patent No.: US 9,469,610 B2
(45) Date of Patent: Oct. 18, 2016

(54) β-LACTAM COMPOUNDS

(75) Inventors: Yvette S. Vaske, Santa Cruz, CA (US);
Maximillian E. Mahoney, Santa Cruz, CA (US); Joseph P. Konopelski, Santa Cruz, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 670 days.

(21) Appl. No.: 13/255,970

(22) PCT Filed: Mar. 15, 2010

(86) PCT No.: PCT/US2010/027340
§ 371 (c)(1),
(2), (4) Date: Sep. 30, 2011

(87) PCT Pub. No.: WO2010/105267
PCT Pub. Date: Jun. 16, 2010

(65) Prior Publication Data
US 2012/0022248 A1    Jan. 26, 2012

Related U.S. Application Data

(60) Provisional application No. 61/210,032, filed on Mar. 13, 2009, provisional application No. 61/225,271, filed on Jul. 14, 2009.

(51) Int. Cl.
*C07D 205/08* (2006.01)
*C07D 207/277* (2006.01)

(52) U.S. Cl.
CPC .......... *C07D 207/277* (2013.01); *C07D 205/08* (2013.01)

(58) Field of Classification Search
CPC .......................... C07D 205/04; C07D 205/08
USPC ..................................... 540/200; 514/210.01
See application file for complete search history.

(56) References Cited

PUBLICATIONS

Gerstenberger, Brian. Org. Lett., vol. 10, No. 3, Jan. 9, 2008.*
Hakimelahi, Gholam. Helvetica Chimica Acta 75 (1992) 1840-1847.*

* cited by examiner

*Primary Examiner* — Golam M M Shameem
*Assistant Examiner* — Laura Daniel
(74) *Attorney, Agent, or Firm* — Adam Warwick Bell; Matthew Rupert Kaser

(57) ABSTRACT

Novel methods for the production of enantiomerically pure (EP) β-lactams by decomposition of α-diazo-β-ketoamides.

16 Claims, 10 Drawing Sheets

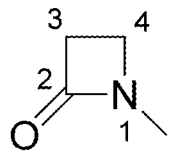
FIG. 1. Basic structure of β-lactam, with standard numbering of the ring system.
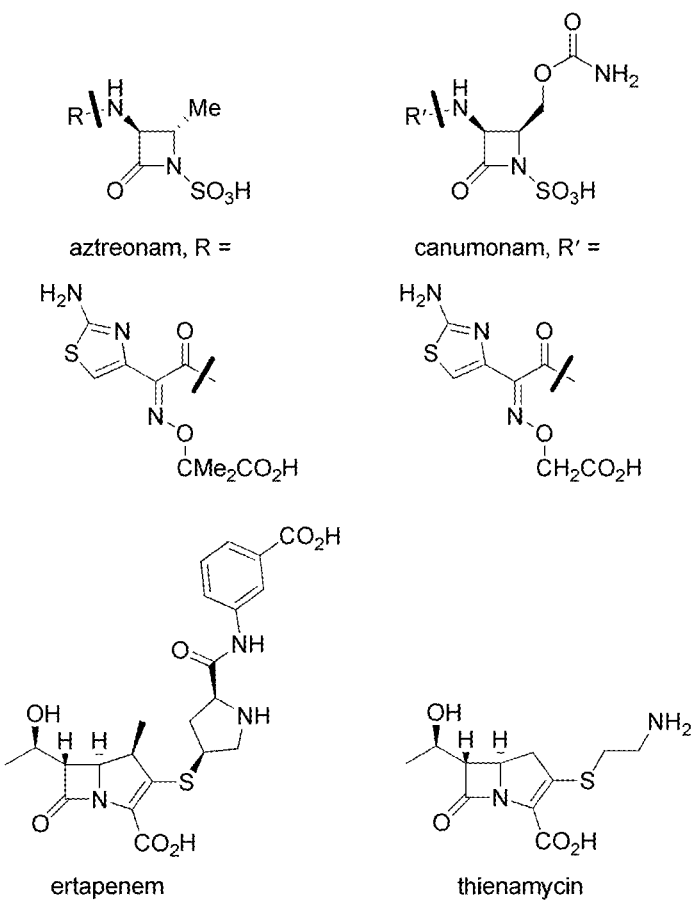
FIG. 2. Clinically used monobactams aztreonam and canumonam, and examples of carbapenem structures ertapenem and thienamycin.

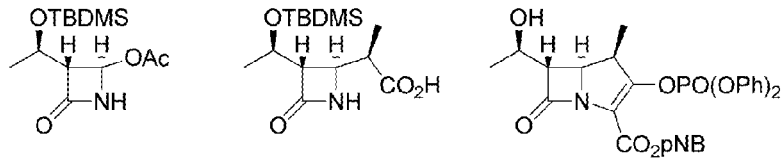
FIG. 3. β-Lactam synthetic intermediates.
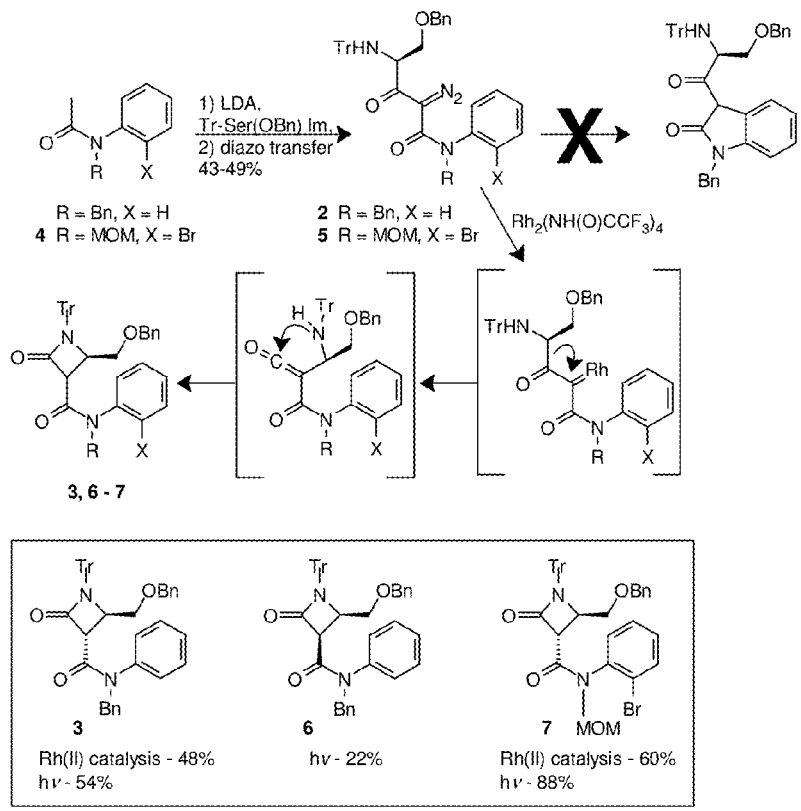
FIG. 4. Transformation of some α-diazo-β-ketoamides to the corresponding β-lactams by rhodium decomposition or photochemistry of the diazo functionality. Taken from *Org. Lett.* 2008, *10*, 369-372.

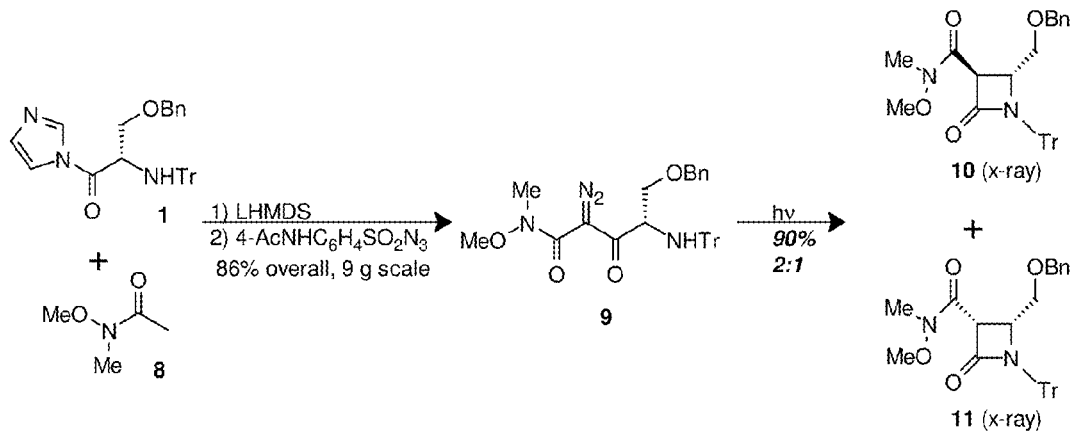

FIG. 5. Compounds made as above by substitution of the acetamide to produce *N*-methoxy-*N* methylacetamide (above) affords high yield of β-lactam structures with the added benefit of easy removal/replacement of the *N*-methoxy-*N*-methyl amide moiety (Weinreb amide) with many other functional groups, lending great versatility to this synthetic approach.
Compounds 9, 10 and 11 are novel compounds.

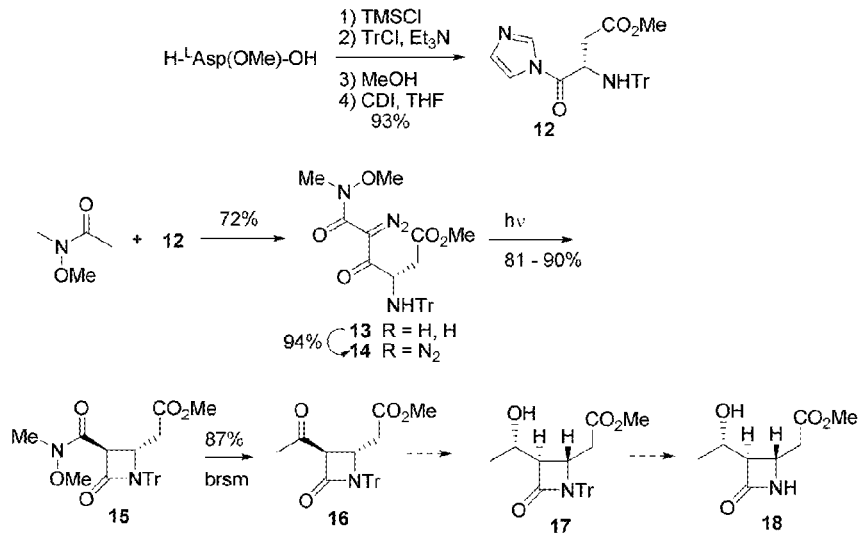

FIG. 6. The method of Hoffman was used for the installation of the trityl group. H-Asp(OMe)-OH is transformed to Tr-Asp(OMe)-Im (12) in 93% overall yield, similar to the combination of literature yields. This figure shows the series of transformations for L-aspartic acid. All numbered compounds in this Figure are novel except for 18.

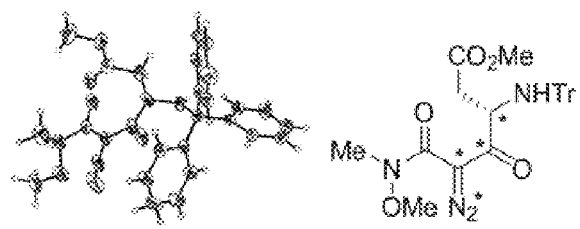
FIG. 7. Solid phase structure of α-diazo-β-ketoamide 9.
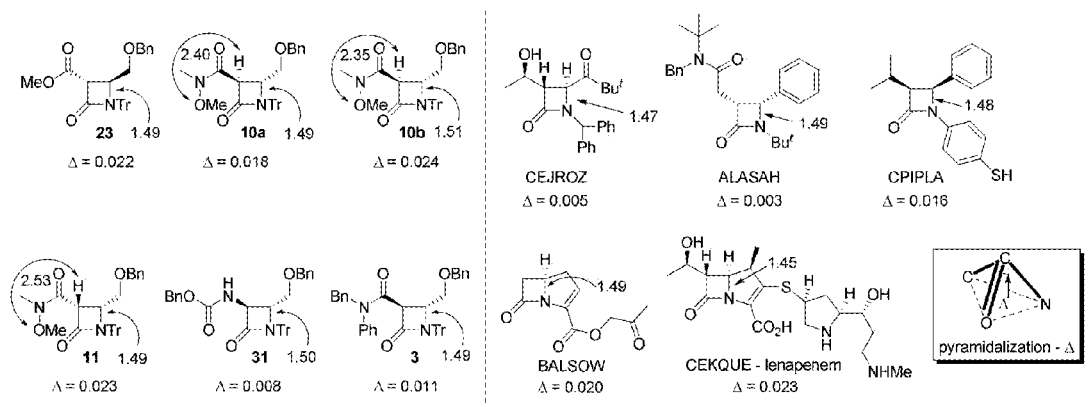
FIG. 8. Bond lengths and distances and pyramidalization (Δ) of *N*-trityl β-lactams from this study (left) and selected beta-lactams from CSD (right). All distances are given in Angstroms (Å). Definition of pyramidalization is shown in box.

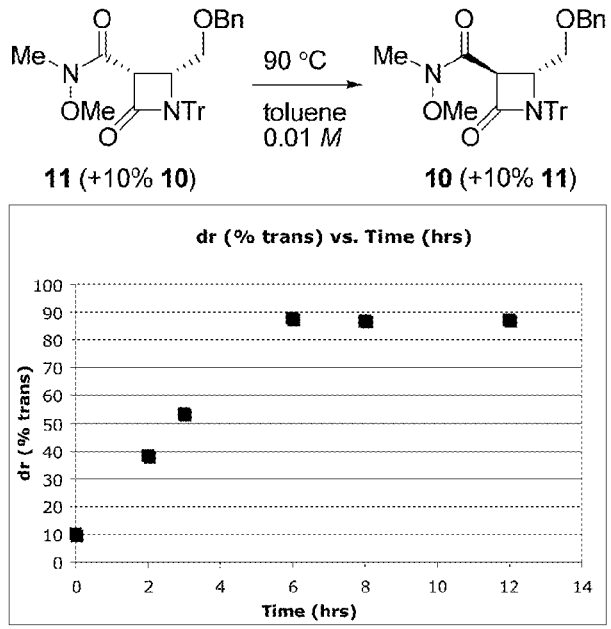
FIG. 9. Thermal epimerization of 11 to 10. Data is obtained by HPLC analysis during the course of the reaction.
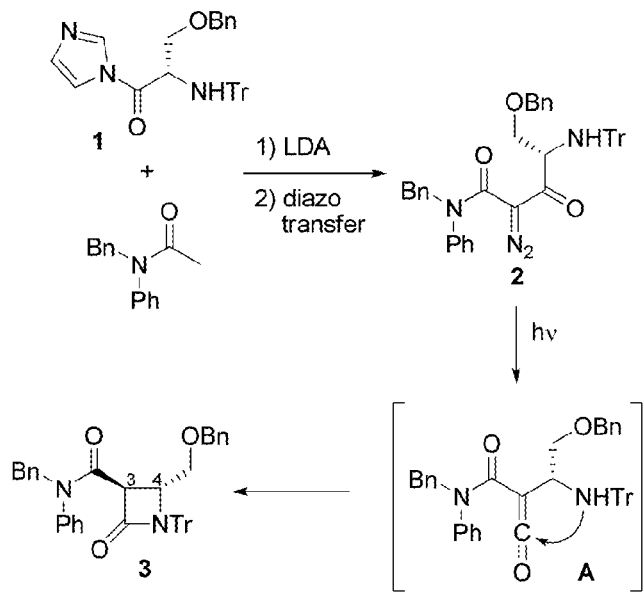
FIG. 10 (also referred to in the specification as Scheme 1) Wolff rearrangement pathway to β-lactams.

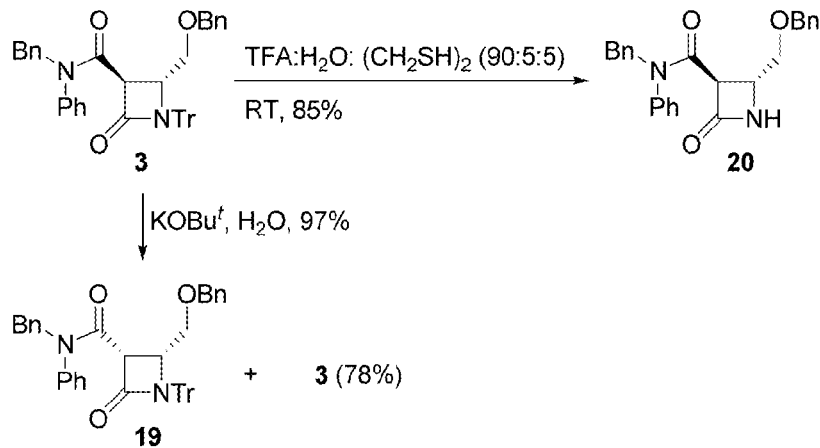
FIG. 11 (also referred to in the specification as Scheme 2). Removal of the trityl group from β-lactam and attempted hydrolysis of C-3 amide functionality. Compounds 19 and 20 are novel.
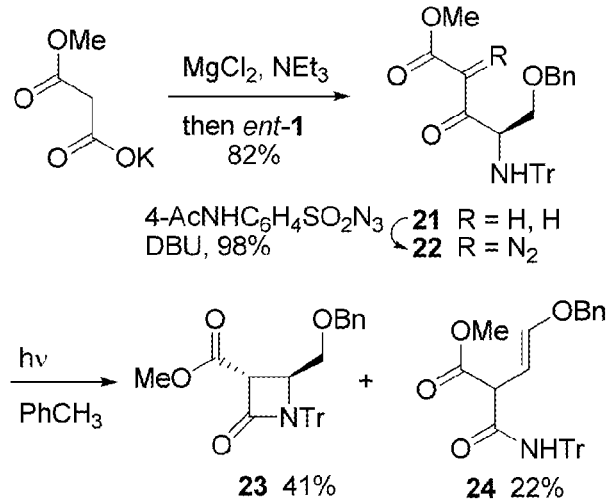
FIG. 12 (also referred to in the specification as Scheme 3). Synthesis and reaction of α-diazo-β-ketoester 7. Compounds 22 and 23 are novel. Others may be novel.

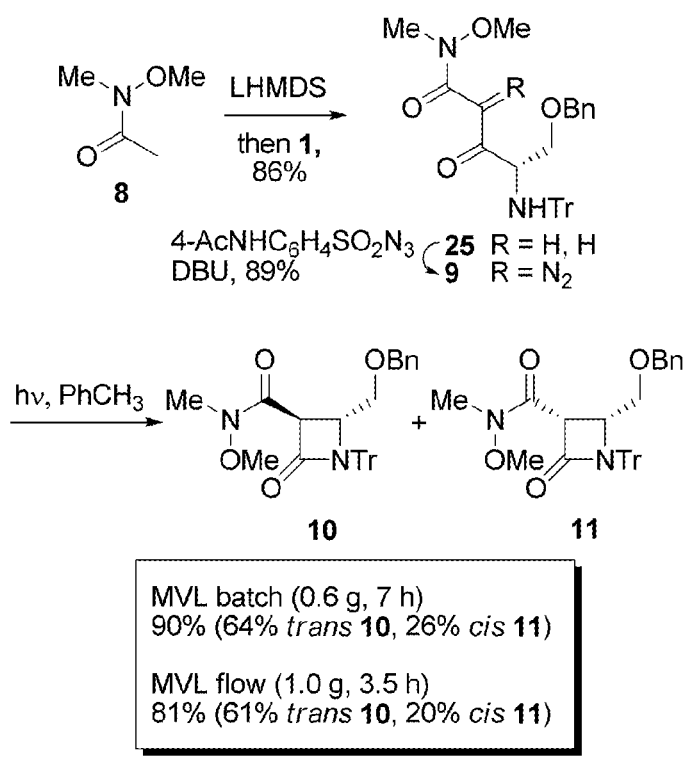
FIG. 13 (also referred to in the specification as Scheme 4). Synthesis and reaction of (Weinreb amide) α-diazo-β-ketoamide 9. Compounds 9, 10 and 11 are novel. Compound 25 may be novel.

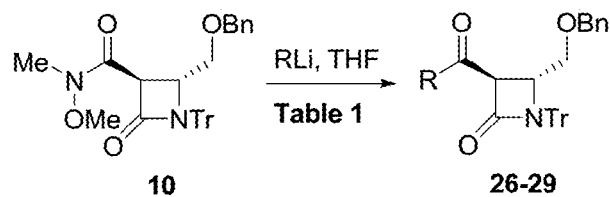
| entry | RLi or RBr; R'Li | Ketone | Yield (%) |
|---|---|---|---|
| 1 | MeLi | 26 | 81 |
| 2 | t-BuLi | 27 | 63 |
| 3 | 4-bromoanisole; n-BuLi | 28 | 78 |
| 4 | 2-bromopropene; t-BuLi | 29 | 62 (79 brsm) |
Compounds 26-29 are novel.
FIG. 14 (also referred to in the specification as Table 1). Ketones from Weinreb amide 10.
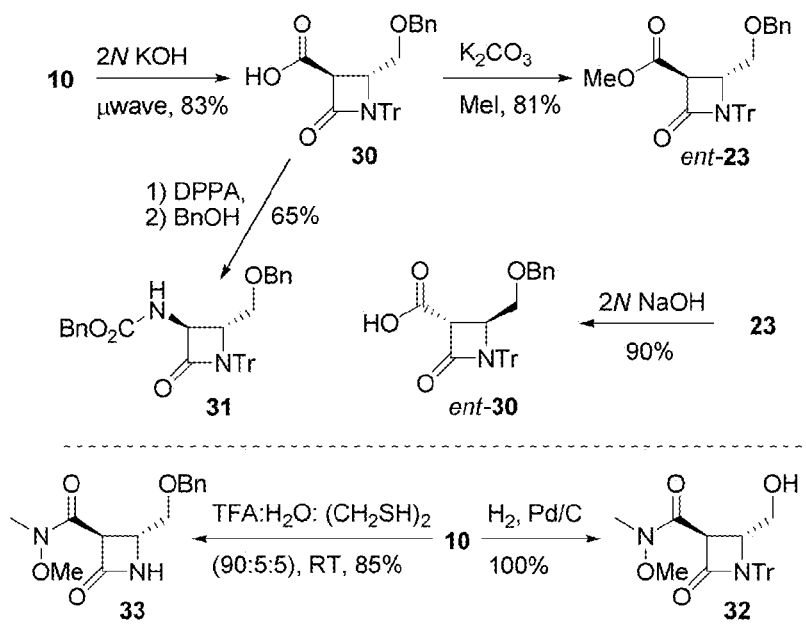
FIG. 15 (also referred to in the specification as Scheme 5). Hydrolysis and Curtius rearrangement. All compounds in Scheme 5 are novel

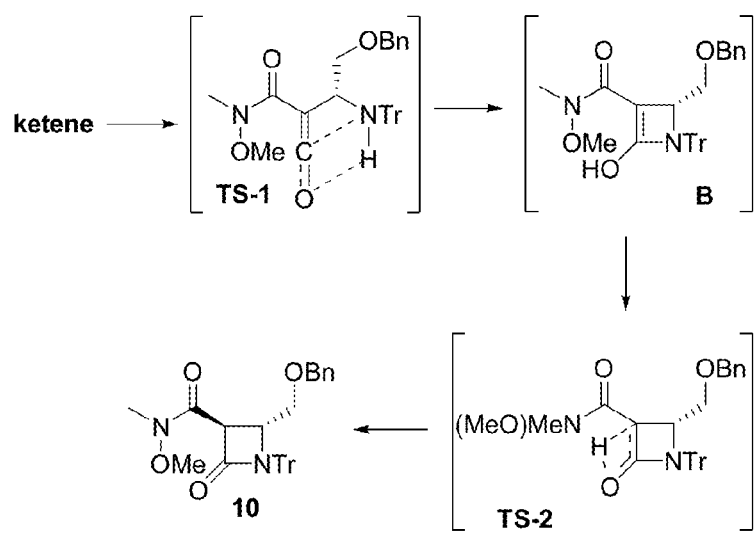
FIG. 16 (also referred to in the specification as Scheme 6). Proposed proton transfer reaction in the formation of β-lactam products.

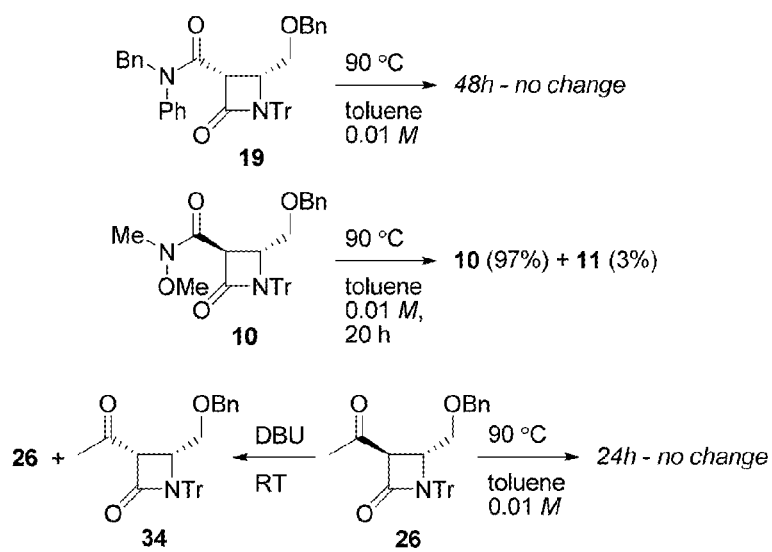
FIG. 17 (also referred to in the specification as Scheme 7). Epimerization studies. Compound 34 is novel.

β-LACTAM COMPOUNDS

RELATIONSHIP TO OTHER APPLICATIONS

This application is a U.S. National Phase Application of PCT Application PCT/US2010/027340 filed under 35 U.S.C. 371 and claims the benefit of and priority to: U.S. Provisional application No. 61210032, filed 13 Mar. 2009, titled "Beta Lactam Compounds", to inventors Joseph Konopelski and Yvette Vaske; and to US Provisional application No. 61225271, filed 14 Jul. 2009, titled "Enantiomerically Pure Beta Lactams", to inventors Joseph Konopelski and Yvette Vaske. All of these applications is hereby incorporated by reference in its entirety for all purposes.

GOVERNMENT SPONSORSHIP

This invention was made with government support under CA98878 awarded by NIH. The government has certain rights in the invention.

FIELD OF THE INVENTION

The invention relates to the synthesis of β-lactam compounds and their intermediaries and derivatives.

BACKGROUND

A β-lactam is a 4-membered ring structure as shown in FIG. 1. The ring is considered to be essential for antibiotic function within the class of antibiotics known as β-lactam antibiotics. The β-lactam antibiotics are divided into subclasses based on additional structural elements. Two classes that the present invention will impact are the monobactams (exemplified by aztreonam and carumonam) and the carbapenems (exemplified by ertapenem) (FIG. 2). In particular, carbapenems are produced by chemical synthesis rather than by fermentation, as is usual for β-lactam antibiotics. The total chemical synthesis of carbapenems was pioneered by Merck scientists in the 1980s during their efforts to produce the natural carbapenem thienamycin. Since the carbapenems have shown themselves to be an important basic structure for antibiotic production, a number of intermediates toward the synthesis of these structures have been commercialized (see FIG. 3).

BRIEF DESCRIPTION OF THE INVENTION

The methodology outlined herein delineates a method to produce enantiomerically pure (EP) β-lactams, their derivatives and differentially substituted EP β-lactams. The power of the technology arises from the unique one step formation of an EP N-trityl β-lactam via a stereospecific intramolecular Wolff rearrangement directly from the corresponding α-amino acid. The use of a Weinreb amide side-chain permits a control element on the C-3 position, allowing ready transformation to other key functionalities. In addition, the N-trityl group, rarely encountered on the β-lactam nucleus, offers superb protection to the strained heterocycle during the course of treatment with reactive nucleophiles such as organolithium reagents and strong base. Incorporation of different amino acid functionalities at the C-4 position of the β-lactam nucleus, as well as diastereomer control provide significant advantages to the method of the invention.

This invention encompasses novel methods for the production of enantiomerically pure (EP) β-lactams by decomposition of α-diazo-β-ketoamides, including but not limited to α-diazo N-methoxy-N-methyl (Weinreb) β-ketoamides. Such amides can be derived from a number of reasonable starting materials, including enantiomerically pure α-amino acids. Decomposition of the α-diazo-β-ketoamides can be accomplished by a number of methods including by photolysis, for example as provided by a light source such as a UV source such as a mercury vapour lamp. Decomposition of the α-diazo-β-ketoamides can also be accomplished by treatment with traditional metal catalysts. The use of light energy to advance the reaction, however, has been shown in the present disclosure to significantly enhance yield and purity of the desired products such as EP trans-β-lactams.

In particular, the invention comprises a novel method for the production of enantiomerically pure (EP) β-lactam compounds, the method comprising performing photolysis of α-diazo-β-ketoamides (including but not limited to α-diazo N-methoxy-N-methyl (Weinreb) β-ketoamides) derived from enantiomerically pure α-amino acids to produce the corresponding EP β-lactam by means of a light-promoted (also referred to in this application as "light-catalysed") intramolecular Wolff rearrangement. The chemistry disclosed herein may be used both with Wienreb amides and non-Weinreb amides. In various embodiments of this light-promoted reaction, the light (electromagnetic) energy for photolysis is provided by a Mercury Vapour Lamp (MVL).

An additional novel feature of this method is that the yield of the reaction product when promoted by light is greater than that when promoted by other means such as metal catalysis. For example the yield of enantiomerically pure β-lactam compounds by the photolysis of α-diazo-β-ketoamides using the methods of the invention may, under various conditions, be greater than 80%, or greater than 82%, 87%, 90% or 93%, which is s considerable improvement over pervious methods.

In other embodiments of the novel methods, the invention includes performing the methods disclosed using a continuous flow reaction for the production of β-lactams by decomposition of α-diazo-β-ketoamides, including but not limited to α-diazo N-methoxy-N-methyl (Weinreb) β-ketoamides. The use of a continuous flow system as disclosed herein is in itself believed to be novel both for the production of enantiomerically pure and non-enantiomerically pure (racemic mixtures of) β-lactams. The use of continuous flow reactors accelerates production making it attractive to produce large amounts of material commercially.

The invention further encompasses a novel method for the transformation of α-diazo-β-ketoamide 2, derived from the amino acid L-serine, to β-lactam 3, using the steps as shown, wherein a stereospecific intramolecular Wolff rearrangement occurs with full retention of absolute configuration, and an intramolecular attack by the trityl protected amine on the intermediate ketene A, produces the β-lactam product. See Scheme 1 that shows the Wolff rearrangement pathway to β-lactams.

In one alternative embodiment the invention encompasses a novel, extremely facile, atom-economical method for the epimerization of the product mixture to the trans isomer, which is generally highly crystalline. This occurs via a C-3 epimerization of Weinreb amide structures via a non-basic, purely thermal route. This purely thermal method is in itself is believed to be novel. In addition, Subsequent transformations of both the Weinreb amide at C-3 (β-lactam numbering) and amino acid side chain at C-4 are well tolerated, allowing for a versatile approach to diverse β-lactam structures.

The invention additionally encompasses a number of novel structures, compounds and mixtures, including previously unknown chemical structures and enantiomerically pure compositions of previously known compounds. The invention also encompasses methods for making and using the aforementioned structures and compositions.

The method of the invention is in itself novel, and allows the synthesis of a number of what are believed to be entirely novel compounds. The method of the invention also produces compositions comprising one or more types of molecule that are novel by virtue of their enantiomeric purity. The novel compounds include the following (the numbers refer to the numerical labelling used throughout this disclosure and in the accompanying figures): Compound 9, Compound 10, Compound 11, Compound 12, Compound 13, Compound 14, Compound 15, Compound 16, Compound 17, Compound 19, Compound 20, Compound 22, Compound 23, Compound 24 (the applicants are less sure of the novelty of compound 24 but to their knowledge it has not been previously disclosed in any publication), Compound 25, Compound 26, Compound 27, Compound 28, Compound 29, Compound 30, Compound 31, Compound 32, Compound 33, and Compound 34. The present invention includes derivatives and variants of all these novel structures.

Additionally the invention encompasses compositions that are novel by virtue of their enantiomeric purity. These include an enantiomerically pure β-lactam having an N-Tr moiety (or a derivative or variants of an N-Tr structure) covalently bonded to at least one of the atoms of the four atom ring structure. The invention includes any such an enantiomerically pure -lactam and derivatives and variants thereof. Such a composition may be pure such that only one enantiomer is detectable, or may be pure to a certain defined degree, such that it can be said to be at least 99.9% pure, 99% pure, 95% pure, 90% pure, 85% pure or 80% pure. In certain specific embodiments the nitrogen of the N-Tr moiety is covalently bonded to two of the carbons of the four atom ring structure. It is believed that the N-Tr group is an important feature in the reactions disclosed herein.

Other novel structures include the precursor compounds (and derivatives and variants thereof) used to make the enantiomerically pure β-lactam compounds of the invention as disclosed in the various figures and schemes.

In certain embodiments one or more phenyl rings of the N-Tr moiety may have substituent groups bonded thereto, but the basic structure of the N-Tr will still be present. Substituent groups may be straight-chain or cyclic, and include phenyl, ether, alkyl, acyl, aryl, carboxyl, amine, amide, alcohol, ketone, amide or other groups including any mentioned in this disclosure. In various preferred embodiments the substituent group will be a net electron donating group and will increase the overall tendency to donate electrons of the N-Tr structure. In other embodiments, the four carbon ring of the β-lactam structure has there-attached, bonded at one vertex to two carbon atoms of the ring, a non-trityl group that is electron donating.

The present disclosure documents the versatility and advantages of the methods of the invention through (a) the facile production of various C-3 functionalities and incorporation of different amino acid side chains, (b) the economy of the route through the direct incorporation of the native α-amino acid into the reaction scheme, (c) the safety of the chemistry that can be performed without the use of metal nor organic catalysis to provide the strained ring system, but rather can be performed with a light source such as a mercury vapour lamp (MVL), and (d) the simplicity of the route that produces high yield of EP trans-β-lactams via a facile epimerization reaction, allowing for easy isolation of the major product by crystallization from the reaction mixture.

Photolysis of α-diazo-β-ketoamides such as α-diazo N-methoxy-N-methyl (Weinreb) β-ketoamides derived from enantiomerically pure (EP) α-amino acids affords the corresponding EP β-lactam via an intramolecular Wolff rearrangement. Photochemistry is promoted by a light source such as a UV source such as a mercury vapour lamp.

A continuous-flow photochemical reactor expedites reaction times and is amenable to scale-up. This equipment in this disclosure may be made from inexpensive and simple laboratory materials.

Diastereoselectivity (cis or trans) of the product β-lactams has been shown to vary from modest to nearly complete. The present invention discloses methods of controlling diastereoselectivity by promoting the production of trans epimers from cis epimers. An extremely facile, atom-economical method for the epimerization of the Weinreb amide product mixture to the trans isomer, generally highly crystalline, has been developed. Subsequent transformations of both the Weinreb amide at C-3 (β-lactam numbering) and amino acid side chain at C-4 are well tolerated, allowing for a versatile approach to produce diverse β-lactam structures.

Advantages of the invention include the production of products that are purer and have less unwanted compounds then those produced by previous methods. Additionally the invention provides higher yield of the product by using photochemistry. Additionally the invention provides significant added benefit of easy removal and/or replacement of the N-methoxy-N-methyl amide moiety (Weinreb amide) with many other functional groups, lending great versatility to this synthetic approach (see figures, schemes and Table 1). Also, the use of continuous flow reactors accelerates production making it attractive to produce large amounts of material commercially. Additionally, the products 10 and 11, which are currently available as a roughly 2:1 mixture from the reaction, can be equilibrated by simple heating to a mixture that favours the trans product 10 by a ratio of 9:1. In addition, the trans product is the more highly crystalline compound of the two, thereby making the isolation of this isomer easier. To our knowledge, the ability of the Weinreb amide to epimerize a chiral centre, without the usual use of base, is unprecedented. We believe that the present invention provides a highly workable route to carbapenem-type building blocks in an attractive number of steps and overall yield. Additionally, this epimerization of the 10/11 mixture to produce 10 as the major product can be performed conventionally with mild base.

BRIEF DESCRIPTION OF THE DRAWINGS, SCHEMES AND TABLES

FIG. 1. Representative β-lactam

FIG. 2. Clinically used monobactams and representative carbapenem structures

FIG. 3. Carbapenem intermediates

FIG. 4. Transformation of some α-diazo-β-ketoamides to the corresponding β-lactams by rhodium decomposition or photochemistry of the diazo functionality (from *Org. Lett.* 2008, 10, 369-372).

FIG. 5. Compounds made as above by substitution of the acetamide to produce N-methoxy-N methylacetamide (above) affords high yield of β-lactam structures with the added benefit of easy removal/replacement of the N-methoxy-N-methyl amide moiety (Weinreb amide) with many other functional groups, lending great versatility to this synthetic approach.

FIG. 6. The method of Hoffman was used for the installation of the trityl group. H-Asp(OMe)-OH is transformed to Tr-Asp(OMe)-Im (12) in 93% overall yield, similar to the combination of literature yields. This figure shows the series of transformations for L-aspartic acid.

FIG. 7. Solid phase structure of α-diazo-β-ketoamide 9.

FIG. 8. Bond lengths and distances and pyramidalization (Δ) of N-trityl β-lactams from this study (left) and selected β-lactams from CSD (right). All distances are given in Angstroms (Å). Definition of pyramidalization is shown in box.

FIG. 9. Thermal epimerization of 11 to 10. Data is obtained by HPLC analysis during the course of the reaction.

FIG. 10 (also referred to in the specification as Scheme 1) Wolff rearrangement pathway to β-lactams.

FIG. 11 (also referred to in the specification as Scheme 2). Removal of the trityl group from β-lactam and attempted hydrolysis of C-3 amide functionality.

FIG. 12 (also referred to in the specification as Scheme 3). Synthesis and reaction of α-diazo-β-ketoester 7.

FIG. 13 (also referred to in the specification as Scheme 4). Synthesis and reaction of (Weinreb amide) α-diazo-β-ketoamide 9.

FIG. 15 (also referred to in the specification as Scheme 5). Hydrolysis and Curtius rearrangement.

FIG. 16 (also referred to in the specification as Scheme 6). Proposed proton transfer reaction in the formation of β-lactam products.

FIG. 17 (also referred to in the specification as Scheme 7). Epimerization studies.

FIG. 14 (also referred to in the specification as Table 1). Ketones from Weinreb amide 10.

GENERAL REPRESENTATIONS CONCERNING THE DISCLOSURE

In this specification, reference is made to particular features of the invention. It is to be understood that the disclosure of the invention in this specification includes all appropriate combinations of such particular features. For example, where a particular feature is disclosed in the context of a particular embodiment or a particular claim, that feature can also be used, to the extent appropriate, in the context of other particular embodiments and claims, and in the invention generally. The embodiments disclosed in this specification are exemplary and do not limit the invention. Other embodiments can be utilized and changes can be made. As used in this specification, the singular forms "a", "an", and "the" include plural reference unless the context clearly dictates otherwise. Thus, for example, a reference to "a part" includes a plurality of such parts, and so forth. The term "comprises" and grammatical equivalents thereof are used in this specification to mean that, in addition to the features specifically identified, other features are optionally present. The term "consisting essentially of" and grammatical equivalents thereof is used herein to mean that, in addition to the features specifically identified, other features may be present which do not materially alter the claimed invention. The term "at least" followed by a number is used herein to denote the start of a range beginning with that number (which may be a range having an upper limit or no upper limit, depending on the variable being defined). For example "at least 1" means 1 or more than 1, and "at least 80%" means 80% or more than 80%. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)—(a second number)", this means a range whose lower limit is the first number and whose upper limit is the second number. Where reference is made in this specification to a method comprising two or more defined steps, the defined steps can be carried out in any order or simultaneously, and the method can optionally include one or more other steps which are carried out before any of the defined steps, between two of the defined steps, or after all the defined steps. Where reference is made herein to "first" and "second" features, this is generally done for identification purposes; unless the context requires otherwise, the first and second features can be the same or different, and reference to a first feature does not mean that a second feature is necessarily present (though it may be present). Where reference is made herein to "a" or "an" feature, this includes the possibility that there are two or more such features (except where the context excludes that possibility).

This specification incorporates by reference all patents, patent applications and documents referred to herein and all documents filed concurrently or previously in connection with this application, including but not limited to such documents which are open to public inspection with this specification.

Definitions

The following abbreviations and terms have the following meanings unless otherwise indicated. It should also be understood that any of the moieties defined forth below may be substituted with a variety of substituents, and that the respective definitions are intended to include such substituted moieties within their scope.

The entirely of the following applications, and particularly the "definitions" sections, are hereby incorporated by reference for all purposes: WO2009114325 (methotrexate adjuvants to reduce toxicity and methods for using the same) and US20060281914 (β-lactam synthesis).

EP stands for enantiomerically pure

Tr or Trt is the trityl group, or triphenylmethyl or —CPh$_3$.

Ph is the phenyl group, or —C$_6$H$_5$ aromatic ring.

Bn is the benzyl group, or —CH$_2$C$_6$H$_5$.

Me is the methyl group, or —CH$_3$.

MOM is the methoxymethyl group, or —CH$_2$OCH$_3$.

t-Bu is the tert-butyl group, or C(CH$_3$)$_3$.

n-Bu is the normal butyl group, or —CH$_2$CH$_2$CH$_2$CH$_3$.

To say that a substance is "pure" may mean that only that substance is detectable in a sample, alternatively it may be pure to a certain defined degree, such that it can be said to be at least 99.9% pure, 99% pure, 95% pure, 90% pure, 85% pure or 80% pure. Unless defined otherwise the term "pure" is used herein to mean at least 80% pure.

The term "yield" when used to refer to a particular chemical reaction, is used to refer to the amount of a particular reactant that is converted to a particular product. Yield if often described as a percentage, for example the reaction A->B may be said to have an 80% yield if 80% of A is converted to B. The reaction A+B->C may be said to have a 90% yield if 90% of A (or B, as specifically defined) is used up to make C.

The term "derivative" or "variant" when applied to one of the structures disclosed herein refers to any structure either synthesised using the disclosed structure as a starting material, or any structure that bears a core structural similarity to the disclosed structure such that a core of the structure can be recognised as being conserved. For example for a β-lactam structure, the core of the β-lactam structure is disclosed in FIG. 1, and any compound bearing this core structure may be said to be a derivative. In the same way, a derivative of any of the novel compounds disclosed herein would encompass any of the disclosed structures that are differentially substituted or wherein aromatic substitution has been performed to provide one or more substituents, and/or wherein another group such as any R group or H, O, OH, CH3, OCH3, CO2CH3, $CH_2C_6H_5$, $C_6H_5$, $OCH_2C_6H_5$, $CH_2OCH_3$, $C(CH_3)_3$, $CH_2CH_2CH_2CH_3$ has been replaced with another group, but wherein the core structure remained the same.

Where substitutions are mentioned, sometimes in connection with variable "R" groups as shown in the figures, the substituent groups may be selected from, for example, the following: hydrogen, substituted or unsubstituted heteroatom, alkyl, alkyl, alkenyl, alkanoyl, aryl, aroyl, aralkyl, alkylamino cycloalkyl, heterocycloalkyl, heteroaryl, or hydroxyl, halogen, azido, fluorophore or polypeptide. In certain embodiments the substituent group may comprise branched or un-branched C1-C18 alkyl, C1-C18 substituted alkyl, C1-C18 alkenyl, C1-C18 acyl, amino, substituted amino, wherein the alkyl, alkenyl or acyl is linear or branched, and optionally substituted with a hydroxyl, an ester and its derivatives, 5 a carboxyl and its derivatives. In a particular embodiment, Any R group may be a lower hydrocarbon substituted with alkoxy, substituted alkoxy, imidate, arylthio, or (substituted aryl)thio. In other embodiments, Any R group may be a lower alkyl selected from methyl, ethyl, propyl, isopropyl, butyl, isobutyl, terabutyl and pentyl. In other embodiments, Any R group may be a lower alkenyl selected from vinyl, substituted vinyl, ethynyl, or substituted ethynyl. In other embodiments, Any R group may be a lower alkanoyl selected from formyl, acetyl, propionyl, isopropionyl, butyryl, isobutyryl, tert-butyryl, valeryl, pivaloyl, caproyl, capryl, lauryl, myristyl, palmityl, stearyl, arachidyl, stilligyl, palmitoyl, oleyl, linolenyl, and arachidonyl. In other embodiments, Any R group may be lower aryl selected from phenyl, p-tolyl, pchlorophenyl, p-aminophenyl, p-nitrophenyl, p-anisyl. In yet other embodiments, Any R group may be a lower aroyl selected from benzoyl and naphthoyl. In other embodiments, Any R group may be a lower aralkyl selected from benzyl, benzhydryl, p-chlorobenzyl, m-chlorobenzyl, p-nitrobenzyl, benzyloxybenzyl, or pentaflourobenzyl. In certain other embodiments, Any R group may be a lower alkylamino is selected from monoalkylamino, monoaralkylamino, dialkylamino, diaralkylamino, and benzylamino.

DETAILED DESCRIPTION OF THE INVENTION

The invention encompasses new methods that use metal decomposition or photolysis of α-diazo-β-ketoamides derived from enantiomerically pure (EP) α-amino acids to produce the corresponding EP β-lactam via an intramolecular Wolff rearrangement. Additionally, the invention encompasses the decomposition of N-methoxy-N-methyl (Weinreb) amides derived from enantiomerically pure (EP) α-amino acids to produce the corresponding EP β-lactam via an intramolecular Wolff rearrangement.

The invention disclosed uses continuous flow reactor, and photochemistry is promoted with standard UV irradiation such as a mercury vapour lamp. Diastereoselectivity (cis or trans) of the product β-lactams is variable. An extremely facile, atom-economical method for the epimerization of the product mixture to the trans isomer, generally highly crystalline, has been developed. Evidence is presented for C-3 epimerization of Weinreb amide structures via a non-basic, purely thermal route. In addition, Subsequent transformations of both the Weinreb amide at C-3 (β-lactam numbering) and amino acid side chain at C-4 are well tolerated, allowing for a versatile approach to diverse β-lactam structures.

A general scheme for the reaction of the invention is shown below, where $R_1$ $R_2$ $R_3$ and $R_4$ represent variable moieties. The asterisk denotes the initial enantiomerically pure center. The term "chiral non-racemic" is used to indicate that the starting material does not need to be a single pure enantiomer. For example, the chemistry would work with, for instance, a 75:25 mixture of compounds that are enantiomeric at the asterisk center, and would produce a 75:25 mixture of products. In an alternative embodiment, the reaction could be performed to produce an enantiomerically pure product. The product in the scheme below includes a second asterisk; this center is induced in the reaction and leads to the mixture of compounds (always about 2:1). For example, the mixture of 10 and 11 would be a 2:1 mixture. Optionally, the chemistry of this system allows us to produce compound 10 in a very pure state by changing 11 to 10 by using either heat or base.

In certain embodiments, the major product of the reaction of the invention is a trans-β-lactam (related to compound 10). For example the product of the reaction may be at least 50%, 60%, 70%, 80%, 90%, 95% or at least 99% trans-β-lactam.

From the present experimental work we believe that the trityl-protected α-diazo-β-ketoamide (e.g., see compound 9) is key to making the β-lactam by this method. To our knowledge, compound 9 has never been previously synthesized and are entirely novel. To our knowledge, a number of other α-diazo-β-ketoamides compounds (such as 12, and 22) are also novel. The present invention includes of derivatives and variants of these novel α-diazo-β-ketoamides.

One publication of interest (Hakimelahi et al, Helvetica Chimica Acta Vol 75, 1992, pages 1840-1847) discloses a short series of cis-β-lactam products possessing an N-Tr or N-CPh$_3$ moiety. These products are racemic mixtures and not enantiomerically pure, thus the product of the reaction is different from the EP product produced by the method of the present invention. Additionally, the process described by Hakimelahi et al. produces the trityl-protected β-lactam by a synthetic route that involves the [2+2] addition of an imine to a ketene in an intermolecular reaction to form the β-lactam ring, a reaction process known as the Staudinger reaction. In this reaction, the initial step is the attack of the nitrogen of the imine onto the ketene central carbon, followed by closure of the 4-membered ring through formation of the C3-C4 bond, generally producing cis product. This is completely different to the reaction described in this invention, in which the trityl-protected α-diazo-β-ketoamide undergoes an exceptionally facile rearrangement with complete retention of the original chiral center to produce a ketene structure that undergoes rapid ring closure. Thus, in the present case the last bond formed in the 4-membered ring molecule is the C—N bond (N1-C2 bond), whereas this is the first bond formed in the Staudinger reaction. In addition, the major product in this invention is the trans isomer, whereas the major product from the publication described above is the cis isomer.

In the scheme below, $R_1$, $R_2$ and $R_3$ may be any suitable moiety, such as, for example, an amide, an alky, aryl, alkoxy, phenyl or aromatic ring structure, or a benzyl group or indeed any group mentioned in the definitions section of this disclosure. The presence of an alkoxy (O-alkyl) group at $R_1$ or $R_2$ would lead to the Weinreb-type amides that are important for various aspects of the invention. To produce a Weinreb amide, either $R_1$ or $R_2$ can be O-alkyl, but not both at the same time.

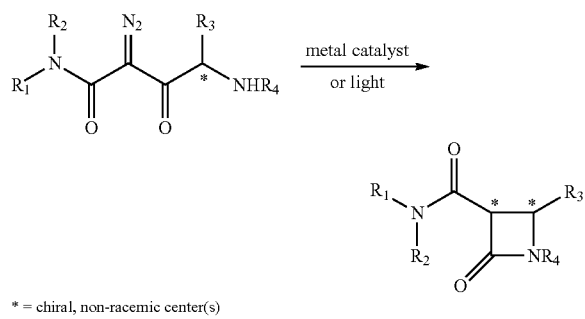

* = chiral, non-racemic center(s)

In the scheme as shown, $R_4$ is an electron-donating group including, but not limited to, triphenylmethyl (also denoted as "Tr" or "trityl" or "C(Ph)$_3$" or "Trt"). There are several different types of trityl groups, including but not limited to those abbreviated Mtt and MMTr, corresponding to (4-methylphenyl)diphenylmethyl and 4-(methoxyphenyl)diphenylmethyl, respectively. There are many other derivatives and variations of the trityl structure possessing two or more phenyl rings, any of which may be present at the $R_4$ position. The protective effect of the trityl group on the α-diazo-β-ketoamide is believed to be an important factor in making the β-lactam by the method of the invention, and it is believed that the use of the trityl group to perform this protective function facilitates the Wolff rearrangement that is necessary for the reaction to proceed.

The basis of the invention is a new synthetic method for producing β-lactam structures that provides a highly workable, commercially attractive route to carbapenem-type building blocks in an attractive number of steps and overall purity and yield. Part of the basic method is described in the inventors' previous publication: "Structural Characterization of an Enantiomerically Pure Amino Acid Imidazolide and Direct Formation of the β-Lactam Nucleus from an α-Amino Acid" Brian S. Gerstenberger, Jinzhen Lin, Yvette S. Mimieux, Lauren E. Brown, Allen G. Oliver, and Joseph P. Konopelski Org. Lett., 2008, 10, 369-372, which is incorporated by reference for all purposes. Building on the original synthetic method the inventors continued further investigations and have been able to show that the reaction is much cleaner (that the products are purer and have less unwanted compounds) and occurs in higher yield if photochemistry is used instead of a chemical (e.g., rhodium) catalyst.

FIG. 5 illustrates that substitution of the original acetamide shown in FIG. 4 as the starting material for N-methoxy-N methylacetamide, affords exceptional yield of β-lactam structures with the significant added benefit of easy removal/replacement of the N-methoxy-N-methyl amide moiety (Weinreb amide) with many other functional groups, lending great versatility to this synthetic approach.

In addition, continuous flow reactors have been developed to accelerate the photochemical reaction and speed up production, making it attractive to produce large amounts of material by this method.

Additionally it was discovered that the products 10 and 11 in FIG. 5, which are available as a roughly 2:1 mixture from the reaction, can be equilibrated by simple heating to a mixture that favors the trans product 10 by a ratio of 9:1. The trans product is the more highly crystalline compound of the two, thereby making the isolation of this isomer easier. The applicants know of no other experiments of this sort, and preliminary data suggest this epimerization reaction to be specific to the Weinreb amide functionality. It is believed that the ability of the Weinreb amide to epimerize a chiral center, without the usual use of base is entirely novel. It is believed that the present invention provides a highly workable route to carbapenem-type building blocks in an attractive number of steps and overall yield.

Further work described herein involves the synthesis of imidazolides such as product 12 (derived from L-aspartic acid, FIG. 6) from the amino acid directly, which allows for both easy adoption of either L- or D-amino acids into this technology and better comparison with existing synthetic schemes by basing this technology on readily available starting materials (FIG. 6).

Also disclosed is the use of the method of Rapoport for the installation of the side chain methyl ester, in which aspartic acid is transformed to H-Asp(OMe)-OH in the same yield as that given in the literature. The method of Hoffman was adapted for the installation of the trityl group and imidazolide functionalities in overall 93% yield from H-Asp(OMe)-OH. FIG. 6 shows the series of transformations for L-aspartic acid. The bottom part of FIG. 6 is essentially identical to FIG. 5, with aspartic acid taking the place of serine in the formation of the key α-diazo-β-keto Weinreb amide 14 and photolysis and epimerization of this compound to give trans isomer 15. Compound 18 is an intermediate toward thienamycin.

EXAMPLES

Overview

The present invention includes the serendipitous transformation of α-diazo-β-ketoamide 2, derived from L-serine, to β-lactam 3 (Scheme 1).[i] The results are consistent with a mechanism involving a stereospecific intramolecular Wolff rearrangement with full retention of absolute configuration.[ii] Intramolecular attack by the trityl protected amine on the intermediate ketene A, formally a disfavoured 4-exo-dig process under Baldwin's rules,[iii,1,iv] affords the product β-lactam. This was unexpected and the art appears to have strongly taught away from this method. Other key observations from this work were (1) the stability and crystallinity of imidazolides such as 1, which translates into handling ease in the sequence; (2) the observation of compound 3 as the major isolable product from rhodium(II) and silver(I) catalysis, and light (somewhat rare,[v] fully expected,[vi] and best yields, respectively); and (3) the stereo specificity of the Wolff rearrangement, as gauged by the clean formation of ent-3 when starting with D-serine.

([1]) For another example of the 4-exo-dig route to β-lactams, see Hachiya, I.; Yoshitomi, T.; Yamaguchi, Y.; Shimizu, M. Org. Lett. 2009, 11, 3266-3268.

EXAMPLES

Synthesis and Related Studies

The applicant's previous work[i] led to the isolation of N-phenyl-N-benzyl amide 3, which, while attractive for initial goals, was deemed cumbersome for manipulation into desired C-3 β-lactam functionalities. For example, treatment of pure 3 with Gassman's "anhydrous hydroxide"[viii] for 24 h resulted in near quantitative recovery of the starting structure, now as an approximately 4:1 trans to cis (19) mixture (Scheme 2). Thus, the trityl group, which has only been explored briefly as a β-lactam ring nitrogen protection group,[viii] offers extreme base stability to the normally reactive β-lactam nucleus. Conversely, treatment with TFA results in removal of the trityl group to give 20 in good yield.

The desire for a more malleable functionality at C-3 led initially to the ester group as a replacement for the fully substituted C-3 amide of 3. The requisite diazo β-ketoester 22 was prepared under mild acylation conditions (Scheme 3).[ix] Adapting a modified procedure,[x] potassium methyl malonate was treated with $NEt_3$ and $MgCl_2$ to form the corresponding magnesium salt, which was subsequently added to a solution of imidazolide ent-1, derived from D-serine. The resulting β-ketoester 21 was obtained in 82% yield. Subsequent treatment with 4-acetamidobenzene sulfonyl azide and DBU gave compound 22 in an overall 80% yield for the two steps. Under standard photochemical conditions compound 22 afforded 63% of a separable mixture of desired trans β-lactam 23 and alkene 24. The structure of β-lactam 23 was confirmed by X-ray crystallography; alkene 24 was assigned by 2D NMR analysis. While the mechanistic pathway for the alkene product is not entirely clear, the new amide functionality clearly suggests that 24 originates from a Wolff rearrangement followed by further reaction.[xi]

The modest yield of β-lactam 23 prompted the search for a C-3 amide functionality that would maintain or exceed the higher product yields encountered in our initial studies while offering facile functional group manipulation. After some consideration, the N-methoxy-N-methyl (Weinreb) amide was chosen for study, as Weinreb amides[xii] hold a reserved place in organic synthesis as valuable and versatile intermediates.[xiii]

Weinreb β-ketoamide 25 was prepared by a modified literature procedure (Scheme 4).[xiv] Accordingly, serine imidazolide 1 was acylated with the lithium enolate (LHMDS) of N-methoxy-N-methyl acetamide to give the desired β-ketoamide 25 in 86% yield on a 9 g scale. Treatment with diazo transfer reagent gave the desired diazo β-ketoamide 9 in 89% yield.

Using standard photolysis conditions, diazo 9 was irradiated with a medium pressure mercury vapor lamp (MVL) and afforded a roughly 2.5:1 easily separable mixture of β-lactams 10 and 11, respectively, in 90% isolated yield. The identity of both β-lactam isomers was confirmed by X-ray crystallography.

To improve upon our processing capabilities, a simple continuous-flow photochemical reactor was devised from common laboratory equipment,[xv] and consisted of the requisite tubing and a low-pressure liquid chromatography pump in addition to standard flasks. External cooling was employed since diazo compounds are, in general, thermally unstable. Accordingly, on a 1 g scale, the reaction was complete in 3.5 h (versus 0.6 g, 7 h for the batch process) to afford an 81% isolated yield and roughly 3:1 separable mixture of 10 and 11, respectively. The improved reaction time and ease of processing material on a larger scale made the modified continuous-flow photochemical process the preferred method, despite slightly diminished yields.[xvi]

What is the origin of the facile Wolff rearrangement of α-diazo-β-ketoamide 9? Optimized yields arise from photochemical decomposition as compared to the use of metal catalysts, and point to a very facile rearrangement reaction. Recent studies on the Wolff rearrangement[xvii] suggest that ketene can form from two different reaction pathways—an extremely rapid rearrangement of the diazo excited state concomitant with nitrogen loss and a slower rearrangement from the ketocarbene after nitrogen loss. The rearrangement is facilitated by the antiperiplanar geometry of the leaving and migrating groups ($N_2$ and amino acid chiral center, respectively), and it is this geometry that is found in the single crystal x-ray study of diazoketone 9 (FIG. 7), derived from aspartic acid. The structure shows the molecule in the s-$Z_K$,s-$E_W$ conformation (K for ketone, W for Weinreb amide), with the dihedral angle defined by $N_2$—C—$C_{C=O}$—$C_\alpha$ (all marked with *) of 172.6°. Thus, the solid-state structure possesses the exact conformation necessary for efficient rearrangement.

To more fully understand the preferred solution conformation of the diazo substrates, hybrid density functional theory calculations of compound 9 were employed. The calculations were performed with no explicit solvent incorporation since the dielectric constant of toluene is very low (D=2.38). Using the crystal structure coordinates of compound 9 as the starting point, four conformations were generated by setting the dihedrals related to the β-dicarbonyl system to either 180° or 0° in recognition of the partial double bond character of these bonds.[ii] These four structures were designated s-$Z_K$,s-$E_W$ (conformation of 9 in the x-ray), s-$Z_K$, s-$Z_W$, s-$E_K$, s-$E_W$,s-$E_K$,s-$Z_W$, with K referring to the conformation around the ketone-diazo carbon bond and W refers to the Weinreb amide-diazo carbon bond. Each of these four conformers was minimized at the RI-PBE/TZVP (P) level of theory.[xviii] Four minimized structures, each residing in the structural space of its starting conformation, were obtained. The calculated lowest energy conformer agrees closely with the x-ray conformer, with no other minimized structure within 15 kJ of the s-$Z_K$,s-$E_W$ conformation. In addition, each structure has one of the trityl group aromatic rings in close facial contact with the α-diazo-β-dicarbonyl functionality. The origin of this close proximity is not understood at the present time and is under investigation.

The Weinreb amide functionality at the C-3 position afforded the opportunity to explore various transformations to highlight the versatility of this functional group within the present structure. In particular, the carbapenem and monobactam classes of antibiotics, exemplified by the structures in FIG. 2, bear the hydroxyethyl and amino functionalities, respectively, at this position of the ring. The former group, a key element in carbapenems of high biological activity, is usually developed via stereocontrolled reduction of the corresponding methyl ketone. Thus, trans-isomer 10 was treated with a series of organolithium reagents and the corresponding C-3 ketones were obtained in good to excellent yields (Table 1). Entries 1 and 2 proceeded directly from the commercially available organolithium reagent. For entries 3 and 4, the organolithium agents were prepared by lithium-halogen exchange using 4-bromoanisolem[xix] and 2-bromopropene,[xx] respectively. Not unexpectedly, the β-lactam carbonyl is fully protected by the large trityl group.

Hydrolysis of trans β-lactam 10 was examined next (Scheme 5). Under microwave-assisted hydrolysis conditions,[xxi] 10 cleanly afforded C-3 carboxylic acid 30 in 83% isolated yield. For comparison, standard ester hydrolysis of trans-isomer 23 afforded ent-30 in 90% yield after purification. Spectral data of the two enantiomeric carboxylic acids were identical and optical rotations were equal in magnitude and opposite in direction. Continuing on the theme of versatility, treatment of C-3 carboxylic acid 30 with diphenylphosphoryl azide[xxii] in the presence of benzyl alcohol afforded the benzyl carbamate 31, the product of the expected Curtius rearrangement (Scheme 5).[xxiii]

The remaining protection groups, those on the C-4 amino acid side chain and the ring nitrogen, were also easily manipulated in an orthogonal manner to the Weinreb amide. Deprotection of the serine side chain is accomplished by standard hydrogenolysis conditions, affording alcohol 32 is near quantitative yield from 10. Deprotection of the ring nitrogen was initially investigated employing the only literature procedure available for a β-lactam N-Tr functionality.[viii] However, this methodology (neat TFA, cat. KClO$_4$) proved capricious in our hands and was abandoned in favor of the reagents employed for the deprotection of 3 (Scheme 1). Under these conditions [TFA/H$_2$O/(CH$_2$SH)$_2$], a reproducible 85% yield of 33 was obtained (Scheme 5).

EXAMPLES

Structural Studies

Having obtained X-ray diffraction data for several of the N-trityl β-lactams prepared in this study, the details of the solid-state structures of these compounds were examined. A β-lactam differs from a normal amide due to the intrinsically strained four-membered ring, which confers decreased amide resonance.[xxiv] For this reason, a monocyclic β-lactam structure exhibits a longer C-2/N (amide) bond length (typically 1.35-1.38 Å vs. 1.33 Å for a normal amide) and shorter C=O bond length (1.21-1.23 Å vs. 1.24 Å for a standard amide).

Data from our structural studies of the N-trityl β-lactams are summarized in FIG. 8 together with β-lactams, including both monocyclic β-lactams (CEJROZ, ALASAH, CPIPLA) and carbapenems (CEKQUE, BALSOW), from the Cambridge Structural Database (CSD, identified by CSD Refcode).[xxv] Select atomic distances (Å) of interest are highlighted in red; pyramidalization at the carbonyl carbon (Δ, Å) is given in blue. Compounds 10a and 10b are two different molecules found in the asymmetric unit cell of the X-ray diffraction data.

Inspection of the structural data revealed that the N-trityl β-lactam C=O bonds were within the expected range for a monocyclic β-lactam, as were the C-2/N(amide) and C-2/C-3 bond length (1.52-1.55 Å). The N/C-4 bond lengths were found to be consistent within the structures defined by this study (1.49-1.51 Å). However, these values, on average, are longer than the corresponding N/C-4 values of the CSD β-lactams (1.45-1.49 Å), and likely arise from the steric interaction of the trityl group with the C-4 substituent. Finally, a consistent close contact between the C-3 proton and the oxygen atom of the Weinreb —OMe group was noted in the structures of 10 and 11.

Pyramidalization (Δ) at the carbonyl carbon of the β-lactam is the perpendicular distance (Å) from the plane defined by the three substituents (FIG. 8, inset).[xxiv,xxvi] A striking feature from these data is that the majority of the N-trityl β-lactams prepared in this work had substantial pyramidalization at the carbonyl carbon (Δ=0.018-0.024 Å) in sharp contrast to most monocyclic β-lactams, which are essentially planar at this center. This trend is highlighted by the CSD structures in FIG. 8, which display large pyramidalizations for the two carbapenem structures (CEKQUE and BALSOW) and smaller non-planarity measurements for the monocyclic β-lactams.

C-3 Stereochemistry and Epimerization

The overall yield of β-lactam product remained consistently high (~90%) throughout the many instances of α-diazo-β-ketoamide 9 photolysis. However, the diastereomeric ratio (dr) of trans-10 to cis-11 varied on a case-by-case basis, always favoring a higher yield of the more thermodynamically stable and highly crystalline trans-isomer. Thus, 10 could be directly isolated from the concentrated crude reaction mixture (toluene) and recrystallized to purity (ethyl acetate/hexanes), thus avoiding the need of column chromatography. However, the isolated yield of the minor product, cis β-lactam 11, varied significantly. Furthermore, despite rigorous column chromatography using various eluting systems, cis-isomer 11 was often accompanied by co-contamination with trans-isomer 10, making isolation of 11 as a single pure compound a challenge. Moreover, this crystalline sample of 11, from which the single crystal was taken for the x-ray structure analysis, epimerized on standing at room temperature in a desiccator from 100% cis to 62% cis over the course of 4 months. The x-ray crystal structure shows no signs of included solvent, which could have facilitated epimerization.

Mechanistically, the Wolff rearrangement route to β-lactams provides the strained ring system and a new chiral center (C-3 of the β-lactam ring) through proton transfer. As first shown in Scheme 1 for the synthesis of 3 and elaborated in Scheme 6 for a synthesis of 10, Wolff rearrangement affords a ketene such as A (Scheme 1). Theoretical work[xxvii] indicates that addition of amines to ketenes occurs via a cyclic transition state (depicted as TS-1, Scheme 6) that forms the corresponding enol amide B as a high energy intermediate. Compound B undergoes intramolecular tautomerization (possibly through TS-2) to afford the final amide product with a new chiral center at C-3. The intramolecular tautomerization, which appears reasonable in the present case given that the photolysis reaction takes place in pure non-protic solvent (toluene) is, nonetheless, likely circumvented by impurities in the system that facilitate the 1,3-proton shift.

Alternatively, this crucial proton transfer could be mediated by a functionality within the molecule, with the serine side chain —OBn group and the Weinreb amide oxygen atoms key possibilities. The solid state epimerization data seemed to support this view, and the proximity of the Weinreb —OMe oxygen to the key C-3 proton in the x-ray structures of 10 and 11 reinforced this idea. Finally, and most importantly, it was discovered that simply heating a 90:10 mixture of 11/10 in toluene at 90° C. for several hours delivers a 90:10 mixture of 10/11 (FIG. 9). No base is added for the transformation. These results are in sharp contrast to the harsh conditions needed to effect epimerization of amide 3 (Scheme 2).

To investigate this transformation more thoroughly, cis isomer 19 and trans isomer 26 were subjected to toluene at 90° C. (Scheme 7); no change in the diastereomer ratio was recorded in either reaction. However, heating pure trans-10 at 90° C. for 20 hours affords a 97:3 mixture of 10 to 11. As was seen in other equilibrium experiments on β-lactam systems, the time to equilibrium is much longer when starting from the more stable trans isomer than from the cis isomer.[xxviii] However, ketone 26 epimerized cleanly to an approximate 2:1 mixture of trans-26 to cis-34, a ratio quite similar to the initial ratio of 10 to 11 (Scheme 4), upon treatment with DBU at room temperature for 18 h. Clearly there are more experiments to perform before suggesting a mechanism for the purely thermal epimerization of 11 to 10. One possibility would be an intramolecular, non-basic epimerization reaction mediated by the Weinreb amide functionality, a previously unknown reaction. However, regardless of the mechanism of the reaction, a facile route to high yields of EP trans β-lactams, and compounds directly related to these systems such as $β^{2,3}$-amino acids, is available.

EXAMPLES

Application of the Method to Produce Carbapenem Products

Thienamycin, shown in FIG. 2, is the direct ancestor to all carbapenem antibiotics. A concise approach to a carbapenem synthetic intermediate would abandon the serine derivatives that dominated our initial development work in favor of aspartic acid. In addition, there was interest in demonstrating a process directly from the amino acid.

Thus, aspartic acid was subjected to the Rapoport protocol[xxix] to provide H-Asp(OMe)-OH in 72% yield without a purification step, identical with the literature (FIG. 6).

Installation of the trityl protection group and imidazolide formation was inspired by the protocols of Hoffman[xxx] and performed without purification to provide highly crystalline 12 in 93% yield from H-Asp(OMe)-OH. Thus, the route from aspartic acid to 12 is accomplished without chromatography in 67% overall yield.

Following the protocols developed for the production of 9 (FIG. 5), the anion of N-methoxy-N-methyl acetamide was reacted with 12 to provide β-ketoamide 13 in 72% yield. Diazo transfer to afford 14 was accomplished in 94% yield through the use of $MsN_3$. Photochemical decomposition of the diazo functionality afforded the expected mixture of trans-15 and the corresponding cis-isomer, which was not isolated. Rather, direct treatment of the mixture in the reaction solution with DBU for 48 hours at room temperature afforded exclusively the desired trans-15 in 81-90% yield from 14 as a crystalline solid.

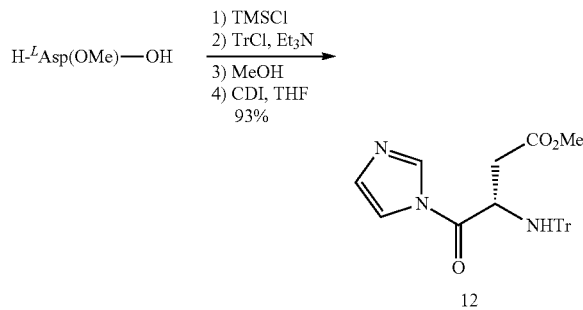

(S)-Methyl 4-(1H-imidazol-1-yl)-4-oxo-3-(tritylamino)butanoate (12). To H-$^L$Asp(OMe)-OH (1.47 g, 10 mmol, 1 equiv) in 18 mL (0.56 M) $CHCl_3/CH_3CN$ (5:1) was added TMSCl and the resulting solution was stirred at reflux for 2 h. The reaction was cooled to room temperature and then placed in an ice bath (0° C.). Triethylamine (2.8 mL, 20 mmol, 2 equiv) was slowly added dropwise and upon complete addition the reaction was permitted to stir for 15 min. TrCl (2.79 g, 10 mmol, 1 equiv) in $CHCl_3$ (10 mL, 1 M) was added dropwise at 0° C., the reaction was permitted to warm to room temperature and stirred overnight. Upon reaction completion 2 mL of MeOH was added and the reaction was stirred for 30 min. The crude mixture was concentrated in vacuo and the residue partitioned between $Et_2O$ and water. The aqueous phase was extracted several times with $Et_2O$. The combined organic phase was washed with brine and dried over $MgSO_4$. The crude reaction was filtered, concentrated and used directly in the subsequent step without purification.

Prior to use, the above crude mixture of Tr-$^L$Asp(OMe)-OH was treated with anhydrous THF and evaporated to dryness several times. The N-trityl protected α-amino acid (1.0 equiv) was subsequently dissolved in 20 mL of THF (0.5 M) and 1.7 g of 1,1'-carbonyldiimidazole (10.5 mmol, 1.05 equiv) was added and stirred for several hours and monitored by TLC. Upon completion, the mixture was concentrated in vacuo and then partitioned between water and $CH_2Cl_2$. The aqueous phase was washed several times with $CH_2Cl_2$ and the combined organics were washed with brine and dried over $MgSO_4$. The crude reaction mixture was purified by either recrystallization from EtOAc/hexanes or passed through a short silica gel plug (40% EtOAc/hexanes) to afford 12 in 4.1 g (93% yield) as a white crystalline solid (recrystallized from EtOAc/hexanes). m.p.=114–115° C.; $[α]_D^{27}=+59.6°$ (c=3.6, $CHCl_3$); $^1H$ NMR (500 MHz, $CDCl_3$) δ 7.71 (s, 1H); 7.45-7.46 (m, 6H); 7.18-7.21(m, 6H); 7.12-7.15 (m, 3H); 7.05 (t, J=1.5 Hz, 1H); 6.90 (dd, J=0.5, 1.5 Hz, 1H); 4.31 (dt, J=6.4, 10.8 Hz, 1H); 3.66 (s, 3H); 3.33 (d, J=10.9 Hz, 1H); 2.88 (dd, J=6.2, 15.2 Hz, 1H); 2.74 (d, J=6.6 15.2 Hz, 1H); $^{13}C$ NMR (125 MHz, $CDCl_3$) δ 171.51, 170.42, 142.25, 136.65, 130.63, 128.79, 128.24, 127.12, 116.38, 71.40, 53.83, 52.39, 41.13; IR (thin film): 3150, 3055, 2952, 1732, 1596, 1491, 1447, 1265, 1206, 1172, 1064, 850, 738, 706 $cm^{-1}$; HRMS=for [M+Na] $C_{27}H_{25}N_3O_3Na$ calcd., 462.17881, found, 462.19035, (Error=24.9614 ppm).

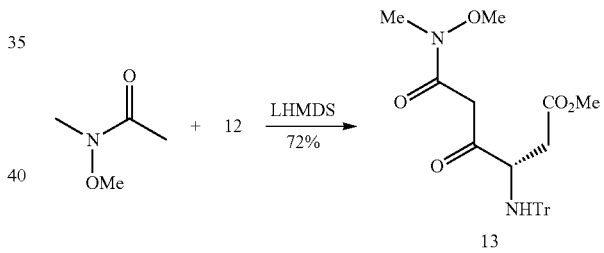

(S)-Methyl 6-(methoxy(methyl)amino)-4,6-dioxo-3-(tritylamino)hexanoate (13). A round bottom flask equipped with a stirbar was charged with $HN(TMS)_2$ (1.8 mL, 8.67 mmol, 3.81 equiv) and THF (4 mL) and was brought to 0° C. (ice/water bath). n-BuLi (3.53 mL of a 2.24 M solution in hexanes, 3.48 equiv) was next added and the mixture was permitted to stir for 1 h. The solution was cooled to −78° C. (acetone/dry ice). In a separate flask, N-methoxy-N-methylacetamide (0.74 mL, 8.00 mmol, 3.52 equiv) in THF (6 mL) was cooled to −78° C. and LHMDS solution (from above) was added via cannula. The resulting anion solution was stirred for 1 h at −78° C. In a separate flask, Tr-$^L$Asp(OMe)-Im (12, 1.0 g, 2.28 mmol, 1.0 equiv) in THF (8 mL, 0.28 M) was cooled to −78° C. and the anion solution was added via cannula to the solution of the amino acid imidazolide. The reaction mixture was warmed to −41° C. ($CH_3CN$/dry ice) and stirred for 45 min. The reaction was quenched with saturated aqueous $NH_4Cl$ and extracted with EtOAc. The combined organics were washed with brine and dried over $Na_2SO_4$. The reaction was filtered and concentrated in vacuo. Purification by silica gel flash column chromatography (20% EtOAc/hexanes) afforded 13 (0.78 g, 72%) as a sticky orange foam and a mixture of keto-enol forms.

$[α]_D^{27}$=9.4 (c=4.7, CHCl$_3$); Reported as a mixture of keto: enol (8:2) forms: $^1$H NMR (500 MHz, CDCl$_3$) δ 13.51 (s, 1H); 7.46-7.53 (m, 6H); 7.14-7.28 (m, 9H); 5.20 (s, 1H); 3.79 (q, J=5.5 Hz, 1H), 3.64 (s, 3H); 3.63 (s, 3H); 3.60 (s, 1H); 3.56 (s, 3H); 3.55 (s, 3H); 3.39 (d, J=8.7 Hz, 1H); 3.26 (d, J=16.2 Hz, 1H); 3.15 (s, 3H); 3.14 (s, 3H); 2.51 (dd, J=4.2, 16.5 Hz, 1H); 2.47 (dd, J=4.3, 15.4 Hz, 1H); 2.22 (dd, J=6.3, 16.4 Hz, 1H); 2.02 (dd, J=7.9, 15.3 Hz, 1H); $^{13}$C NMR (125 MHz, CDCl$_3$) δ 205.71, 176.86, 172.04, 171.82, 168.07, 146.56, 146.441, 146.18, 128.97, 128.19, 128.07, 126.86, 126.64, 87.05, 71.43, 61.48, 59.55, 54.33, 51.94, 51.64, 45.13, 38.86, 37.80, 32.11; IR (thin film): 3057, 2950, 1732, 1659, 1595, 1489, 1447, 1438, 1358, 1266, 1204, 1113, 902, 775, 736, 708 cm$^{-1}$; HRMS [M+K] for C$_{28}$H$_{30}$N$_2$O$_5$K, calcd., 513.17863, found, 513.17760 (Error=2.0105 ppm).

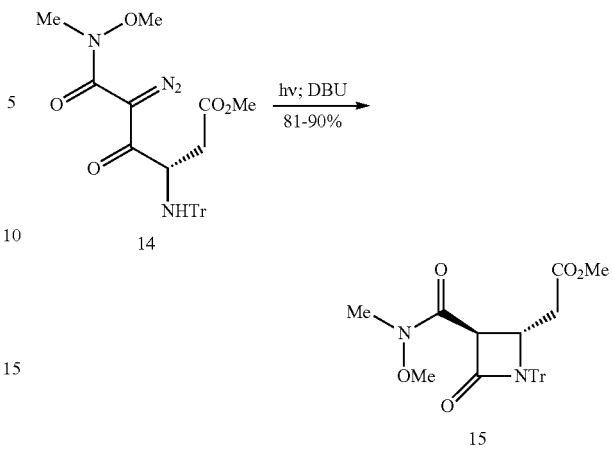

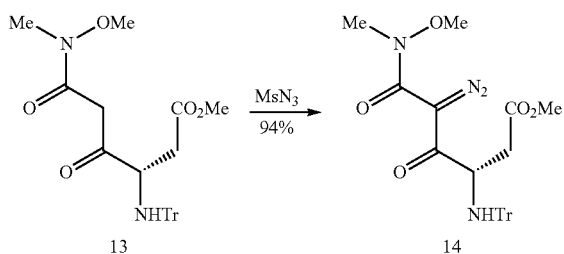

(S)-Methyl 5-diazo-6-(methoxy(methyl)amino)-4,6-dioxo-3-(tritylamino)hexanoate (14). β-ketoamide 13 (3.70 g, 7.80 mmol, 1.0 equiv) was dissolved in 20.0 mL of acetonitrile (0.37 M) and H$_2$O (0.14 mL, 1.0 equiv). Diazo transfer reagent, MeSO$_2$N$_3$ (1.02 mL, 11.70mmol, 1.5 equiv) and 1,8-Diazabicyclo[5.4.0]undec-7-ene (1.75 mL, 11.70 mmol, 1.5 equiv) were sequentially added. The resulting reaction mixture was permitted to stir for 4 h and then this reaction mixture was diluted with diethyl ether. The organic phase was washed sequentially with 10% NaOH, water, and brine. The organic phase was dried over anhydrous magnesium sulfate, filtered and then concentrated in vacuo. The oil was diluted in 1/1 ethyl acetate/hexanes and loaded onto a small plug of silica. The plug was eluted with 1/1 ethyl acetate/hexanes and the organics concentrated to provide the pure product 14 as a pale yellow foam (3.67 g) representing a 94% yield. X-ray quality crystals were grown from EtOAc/hexanes. m.p.=130–131° C.; $[α]_D^{27}$=−68.4° (c=4.3, CHCl$_3$); $^1$H NMR (500 MHz, CDCl$_3$) δ 7.47-7.49 (m, 6H); 7.19-7.22 (m, 6H), 7.13 (tt, J=1.6, 7.3 Hz, 3H), 4.88 (dt, J=5.7, 11.1 Hz, 1H), 3.68 (s, 3H); 3.60 (s, 3H); 3.11 (s, 3H), 2.74 (dd, J=6.1, 13.8 Hz, 1H); 2.61 (dd, J=6.1, 13.8 Hz, 1H); $^{13}$C NMR (125 MHz, CDCl$_3$) δ 193.74, 161.01, 145.24, 128.04, 126.72, 125.31, 70.06, 60.18, 55.19, 50.77, 39.07, 32.65; IR (thin film): 3057, 2948, 2118, 1736, 1638, 1596, 1490, 1461, 1447, 1373, 1267, 1192, 1162, 1113, 1028, 940, 904, 776, 736, 706, 644 cm$^{-1}$; HRMS [M+Na] for C$_{28}$H$_{28}$N$_4$O$_5$Na, calcd., 523.19519, found, 523.19997 (Error=9.1333 ppm).

Method A—Mercury Vapor Lamp Flow Method: Fluorinated Ethylene Propylene (FEP) tubing (33 m, 1.6 mm i.d.×3.2 mm o.d) with solvent volume capacity of 100 mL was used and equipped with a medium-pressure liquid chromatography pump (FMI "Q" Pump). The LC pump flow rate was set to 12.5 mL/min. A three-neck Pyrex round bottom flask was charged with diazo 14 (2.58 g, 5.15 mmol) and 515 mL of toluene (0.01 M), which was degassed prior to use by bubbling N$_2$ for 1 h. To one of the joints of the three-neck round bottom flask, N$_2$ was bubbled throughout the course of the reaction. The other two joints were equipped with modified septa having exit tubing to the LC pump and receiving tubing from the pump and photochemical reactor. Throughout the course of the reaction the three-neck flask was externally cooled by ice/NaCl bath. For the photochemical reactor, a hollow pyrex glass tube was wrapped (2.5 layers) with 47 coils of FEP tubing. The assembly was cooled in a dewar with NaCl/ice (−5° C.) bath. The immersion well with the medium pressure mercury vapor lamp was carefully placed inside the above hollow cavity of the pyrex glassware. Product formation from the continuous-flow photochemical reactor was monitored by TLC (40% EtOAc/hexanes). After 3.5 h the reaction was stopped and 100 mL of toluene was added to rinse the FEP tubing. Subsequently, epimerization of the crude photochemical mixture was achieved employing 3.85 mL of 1,8-diazabicyclo[5.4.0]undec-7-ene (DBU, 25.75 mmol, 5 equiv); the resulting solution was permitted to stir at room temperature for 48 h. The reaction was passed through a plug of silica gel (vacuum filtration) and was washed with a minimal amount of toluene. The silica gel was next washed with EtOAc and was collected in a separate flask. The EtOAc organic phase was concentrated and the residue was triturated with hexanes. The solvent was decanted and the white solid was recrystallized from EtOAc/hexanes to afford 1.97 g (81% yield) of trans β-lactam 15 as a white solid.

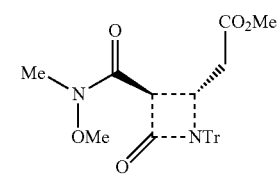

Methyl 2-[(2S,3S)-3-(methoxy(methyl)carbamoyl)-4-oxo-1-tritylazetidin-2-yl]acetate (15): m.p.=168–169° C.;

[α]$_D^{27}$=+23.3° (c=3.6, CHCl$_3$); $^1$H NMR (600 MHz, CDCl$_3$): δ 7.28-7.35 (m, 15H); 4.55 (d, J=9.9 Hz, 1H); 4.35 (s, 1H); 3.79 (s, 3H); 3.55 (s, 3H); 3.29 (s, 3H); 2.19 (dd, J=10.5 16.1 Hz, 1H); 1.78 (dd, J=3.4, 16.1 Hz, 1H); $^{13}$C NMR (125 MHz, CDCl$_3$): δ 170.45, 166.99, 163, 39, 141.92, 129.92, 129.78, 128.37, 128.33, 128.23, 127.85, 127.74, 74.37, 62.56, 56.04, 53.15, 51.97, 37.43, 32.49; IR (thin film): 3059, 2951, 1755, 1738, 1655, 1492, 1444, 1368, 1198, 1180, 1157, 992, 754, 735, 701, 633 cm$^{-1}$; HRMS [M+H] for $C_{28}H_{29}N_2O_5$, calcd., 473.20710, found, 473.20895 (Error=3.9120 ppm).

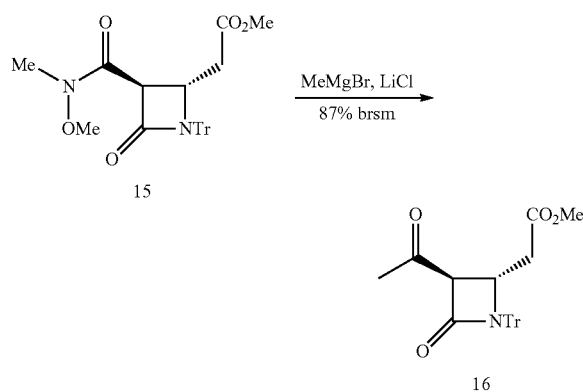

Methyl 2-((2S,3S)-3-acetyl-4-oxo-1-tritylazetidin-2-yl)acetate (16). Oven-dried LiCl (0.276 g, 6.511 mmol, 7.3 equiv) was vigorously stirred in THF (9.0 mL) until fully dissolved. Trans β-lactam 15 (0.420 g, 0.889 mmol, 1.0 equiv) was added and cooled to 0° C. A solution of MeMgBr (0.98 mL, 0.987 mmol, 1.1 equiv, 1M THF) was added dropwise and stirred at 0° C. for 2 h, at which time the ice-bath was removed and the reaction allowed to slowly warm to room temperature. After stirring for 48 h sat. NHCl$_{(aq)}$ was added to quench the reaction, which was further diluted with EtOAc. The organics were washed with water, followed by brine and dried over Na$_2$SO$_4$. The organics were concentrated in vacuo and purified by flash column chromatography (35% EtOAc/hexanes) to provide the pure ketone 16 (R$_f$=0.32, 0.135 g, 36% yield) and recovered starting material 15 (R$_f$=0.16, 0.249 g) representing an 87% yield (based on recovered starting material, brsm). m.p.=52-54° C.; [α]$_D^{23}$=+71.875° (c=0.8, MeOH); $^1$H NMR (500 MHz, CDCl$_3$): δ 7.31-7.36 (m, 9H); 7.20-7.22 (m, 6H); 5.41 (ddd, J=2.2, 3.5, 10.3 Hz, 1H); 4.03 (d, J=2.1 Hz, 1H); 3.57 (s, 3H); 2.36 (s, 3H); 2.13 (dd, J=10.3, 16.2 Hz, 1H); 1.73 (dd, J=3.5, 16.2 Hz, H); $^{13}$C NMR (125 MHz, CDCl$_3$): δ 200.04, 170.45, 163.17, 141.83, 129.82, 128.26, 128.00, 74.54, 66.68, 52.01, 52.01, 37.15, 30.70; IR (thin film): 3059, 2953, 1759, 1714, 1597, 1493, 1444, 1359, 1337, 1177, 1034, 752, 700, 639 cm$^{-1}$; HRMS for [M+Na] $C_{27}H_{25}NO_4Na$ calc'd., 450.16758, found, 450.16980 (Error=4.9322 ppm).

REFERENCES

All documents and publications referred to in this disclosure and hereby incorporated by reference for all purposes.

($^i$) Gerstenberger, B. S.; Lin, J.; Mimieux, Y. S.; Brown, L. E.; Oliver, A. G.; Konopelski, J. P. Org. Lett. 2008, 10, 369-372.

($^{ii}$) Kirmse, W. Eur. J. Org. Chem. 2002, 2193-2256.

($^{iii}$) Baldwin, J. E. J. Chem. Soc. Chem. Comm. 1976, 734-736

($^{iv}$) The possibility of this type of ketene addition reaction in the biosynthesis of carbapenems has recently been discussed: Raber, M. L.; Castillo, A.; Greer, A.; Townsend, C. A. ChemBioChem 2009, 10, 2904-2912.

($^v$) Davies, J. R.; Kane, P. D.; Moody, C. J.; Slawin, A. M. Z. J. Org. Chem. 2005, 70, 5840-5851, and references therein.

($^{vi}$) Podlech, J.; Seebach, D. Liebigs Ann. 1995, 1217-1228.

($^{vii}$) Gassman, P. G.; Hodgson, P. K. G.; Balchunis, R. J. J. Am. Chem. Soc. 1976, 98, 1275-1276.

($^{viii}$) Hakimelahi, G. H.; Shiao, M.-J.; Hwu, J. R.; Davari, H. Helv. Chim. Acta 1992, 75, 1840-1847.

($^{ix}$) Brooks, D. W.; Lu, L. D. -L; Masamune, S. Angew. Chem. Int. Ed. Engl. 1979, 18, 72-74.

($^x$) Mai, A, Sbardella, G, Artico, M, Ragno, R, Massa, S, Novellino, E, Greco, G, Lavecchia, A, Musiu, C, La Colla, M.; Murgioni, C.; La Colla, P.; Loddo, R. J. Med. Chem. 2001, 44, 2544-2554.

($^{xi}$) For alkene formation accompanying Wolff rearrangement, see Stork, G.; Szajewski, R. P. J. Am. Chem. Soc. 1974, 96, 5787-5791.

($^{xii}$) Nahm, S.; Weinreb, S. M. Tetrahedron Lett. 1981, 22, 3815-3818.

($^{xiii}$) (a) For a recent review, see: Balasubramaniam, S.; Aidhen, I. S. Synthesis 2008, 3707-3738.

($^{xiv}$) Kulesza, A.; Ebetino, F. H.; Mazur, A. W. Tetrahedron Lett. 2003, 44, 5511-5514.

($^{xv}$) (a) For a recent review, see: Wiles, C.; Watts, P. Eur. J. Org. Chem. 2008, 1655-1671. (b) Lainchbury, M. D.; Medley, M. I.; Taylor, P. M.; Hirst, P.; Dohle, W.; Booker-Milburn, K. I. J. Org. Chem. 2008, 73, 6497-6505. (c) Hook, B. D. A.; Dohle, W.; Hirst, P. R.; Pickworth, M.; Berry, M. B.; Booker-Milburn, K. I. J. Org. Chem. 2005, 70, 7558-7564.

($^{xvi}$) See Supporting Information for experimental details and FIG. S1 for a picture of the continuous-flow photochemical reactor.

($^{xvii}$) Burdzinski, G. T.; Wang, J.; Gustafson, T. L.; Platz, M. S. J. Am. Chem. Soc. 2008, 130, 3746-3747.

($^{30}$) Neese, F., ORCA—an ab initio, Density Functional and Semiempirical program package, Version 2.6.35 University of Bonn, 2008.

($^{xix}$) Jones, R. G.; Gilman, H. Chem. Rev. 1954, 54, 835-890.

($^{xx}$) (a) Fuller, N. O.; Morken, J. P. Org. Lett. 2005, 7, 4867-4869. (b) Ebel, H.; Zeitler, K.; Steglich, W. Synthesis 2003, 101-106.

($^{xxi}$) Jaipuri, F. A.; Jofre, M. F.; Schwarz, K. A.; Pohl, N. L. Tetrahedron Lett. 2004, 45, 4149-4152.

($^{xxii}$) Shioiri, T.; Ninomiya, K.; Yamada, S.-i. J. Am. Chem. Soc. 1972, 94, 6203-6205.

($^{xxiii}$) Gómez-Sánchez, E.; Marco-Contelles, J. Tetrahedron 2005, 61, 1207-1219.

($^{xxiv}$) Page, M. I. The Chemistry of β-Lactams; Blackie Academic & Professional: Glasgow, 1992; Chapter 2.

($^{xxv}$) Allen, F. H. Acta Cryst. 2002, B58, 380-388.

($^{xxvi}$) Lwowski, W. In Comprehensive Heterocyclic Chemistry, Pergamon Press: Oxford, 1964; Vol. 7, Part 5; p 300-301.

($^{xxvii}$) Cannizzaro, C. E.; Houk, K. N. J. Am. Chem. Soc. 2004, 126, 10992-11008, and references therein.

($^{xxviii}$) Bose, A. K.; Narayanan, C. S.; Manhas, M. S. Chem. Commun. 1970, 975-976.

($^{xxix}$) Gmeiner, P.; Feldman, P. L.; Chu-Moyer, M. Y.; Rapoport, H. J. Org. Chem. 1990, 55, 3068-3074.

(ⁿⁿⁿ) Hoffman, R. V.; Maslouh, N.; Cervantes-Lee, F. *J. Org. Chem.* 2002, 67, 1045-1056.

The invention claimed is:

1. A composition comprising an enantiomerically pure β-lactam having an N-Tr moiety, wherein the nitrogen of said N-Tr moiety is covalently bonded to two of the carbons of the four-atom ring structure wherein the enantiomerically pure β-lactam consists essentially of one of the following:

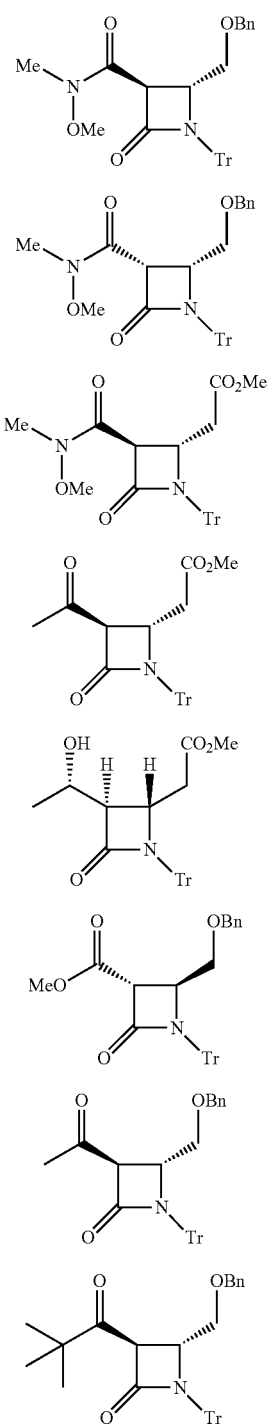

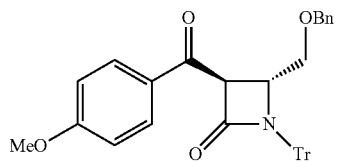

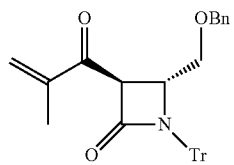

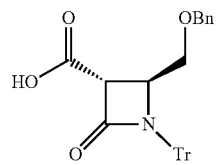

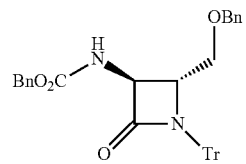

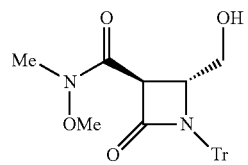

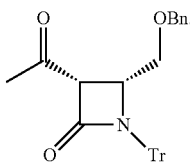

2. A composition comprising an enantiomerically pure β-lactam wherein the enantiomerically pure β-lactam consists of compound 34 as shown below:

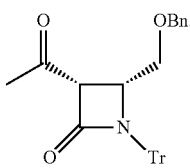

3. The composition of claim 1 wherein the enantiomerically pure β-lactam consists essentially of Compound 10.
4. The composition of claim 1 wherein the enantiomerically pure β-lactam consists essentially of Compound 11.
5. The composition of claim 1 wherein the enantiomerically pure β-lactam consists essentially of Compound 15.
6. The composition of claim 1 wherein the enantiomerically pure β-lactam consists essentially of Compound 16.
7. The composition of claim 1 wherein the enantiomerically pure β-lactam consists essentially of Compound 17.

8. The composition of claim 1 wherein the enantiomerically pure β-lactam consists essentially of Compound 23.

9. The composition of claim 1 wherein the enantiomerically pure β-lactam consists essentially of Compound 26.

10. The composition of claim 1 wherein the enantiomerically pure β-lactam consists essentially of Compound 27.

11. The composition of claim 1 wherein the enantiomerically pure β-lactam consists essentially of Compound 28.

12. The composition of claim 1 wherein the enantiomerically pure β-lactam consists essentially of Compound 29.

13. The composition of claim 1 wherein the enantiomerically pure β-lactam consists essentially of Compound 30.

14. The composition of claim 1 wherein the enantiomerically pure β-lactam consists essentially of Compound 31.

15. The composition of claim 1 wherein the enantiomerically pure β-lactam consists essentially of Compound 32.

16. The composition of claim 1 wherein the enantiomerically pure β-lactam consists essentially of Compound 34.

* * * * *